United States Patent [19]

Harada et al.

[11] Patent Number: 4,521,340

[45] Date of Patent: Jun. 4, 1985

[54] PHARMACEUTICALLY ACCEPTABLE SALTS OF THE ANTIBIOTIC C-19393 $E_5$

[75] Inventors: Setsuo Harada, Kawanishi; Susumu Shinagawa, Higashiosaka; Kazuaki Kitano, Sakai, all of Japan

[73] Assignee: Takeda Chemical Industries, Ltd., Osaka, Japan

[21] Appl. No.: 316,903

[22] Filed: Oct. 30, 1981

[30] Foreign Application Priority Data

Dec. 26, 1980 [JP] Japan .................................. 55-185450

[51] Int. Cl.$^3$ ........................................... C07D 487/04
[52] U.S. Cl. .............................................. 260/245.2 T
[58] Field of Search .................................... 260/295.2 T

[56] References Cited

U.S. PATENT DOCUMENTS

| | | | |
|---|---|---|---|
| 4,141,986 | 2/1979 | Cassidy et al. | 260/295.2 T |
| 4,162,323 | 7/1979 | Kahan | 260/245.2 T |
| 4,211,707 | 7/1980 | Ratcliffe | 260/245.2 T |
| 4,278,686 | 7/1981 | Corbett et al. | 424/114 |
| 4,415,997 | 11/1983 | Nakayama et al. | 260/245.2 T |

FOREIGN PATENT DOCUMENTS 3003624  11/1980  Fed. Rep. of Germany ... 260/245.2 T

OTHER PUBLICATIONS

J.C.S. Perkin Transaction I., pp. 403-411 (1983), Natsugari et al.
Harada et al.; Tetrahedron, vol. 39, No. 1, pp. 75-82 (1983).
J. of Antibiotics, vol. XXXII; (9/1979) pp. 961-963.

*Primary Examiner*—Mary C. Lee
*Attorney, Agent, or Firm*—Wenderoth, Lind & Ponack

[57] ABSTRACT

Novel antibiotic C-19393 $E_5$, which is produced by cultivating a microorganism belonging to the genus Streptomyces, has strong antimicrobial activity against gram-positive and gram-negative bacteria and, thus, are useful as a bactericide or disinfectant.

1 Claim, 2 Drawing Figures

PHARMACEUTICALLY ACCEPTABLE SALTS OF THE ANTIBIOTIC C-19393 E₅

This invention relates to Antibiotic C-19393 E$_5$, a new β-lactam antibiotic compound, which has the formula (I):

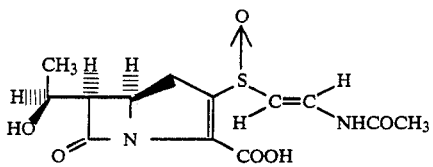

and the salts thereof and to a method for producing said antibiotic and salts. The present inventors previously discovered and developed Antibiotic C-19393 S$_2$ and Antibiotic C-19393 H$_2$, both of which are novel β-lactam antibiotics, and methods for producing them. These antibiotics and methods were described and claimed in Japanese Patent Laid-open Nos. 104296/1980 and 5496/1981. Thereafter, the present inventors discovered in the fermentation broths of C-19393 S$_2$- and C-19393 H$_2$- producing strains a new antibiotic compound which was quite distinct from said antibiotics, and designated it Antibiotic C-19393 E$_5$. Following that discovery, the inventors sought for a commercially useful method of producing Antibiotic C-19393 E$_5$ and have ultimately developed the present invention.

The present invention is directed to:
(1) Antibiotic C-19393 E$_5$, inclusive of its salts;
(2) a method for producing Antibiotic C-19393 E$_5$ characterized by cultivating a C-19393 E$_5$- producing strain of the genus Streptomyces in a culture medium to cause the strain to elaborate and accumulate C-19393 E$_5$ in the resultant culture broth and harvesting the same antibiotic; and
(3) a method according to (2) wherein said C-19393 E$_5$-producing strain is a strain which does not give normal growth on a medium containing inorganic sulfates as exclusive sources of sulfur but gives normal growth in the presence of at least one member selected from the group consisting of thiosulfates, cysteine and methionine.

Hereinafter, Antibiotic C-19393 E$_5$ will sometimes be referred to briefly as C-19393 E$_5$.

Figure 1:
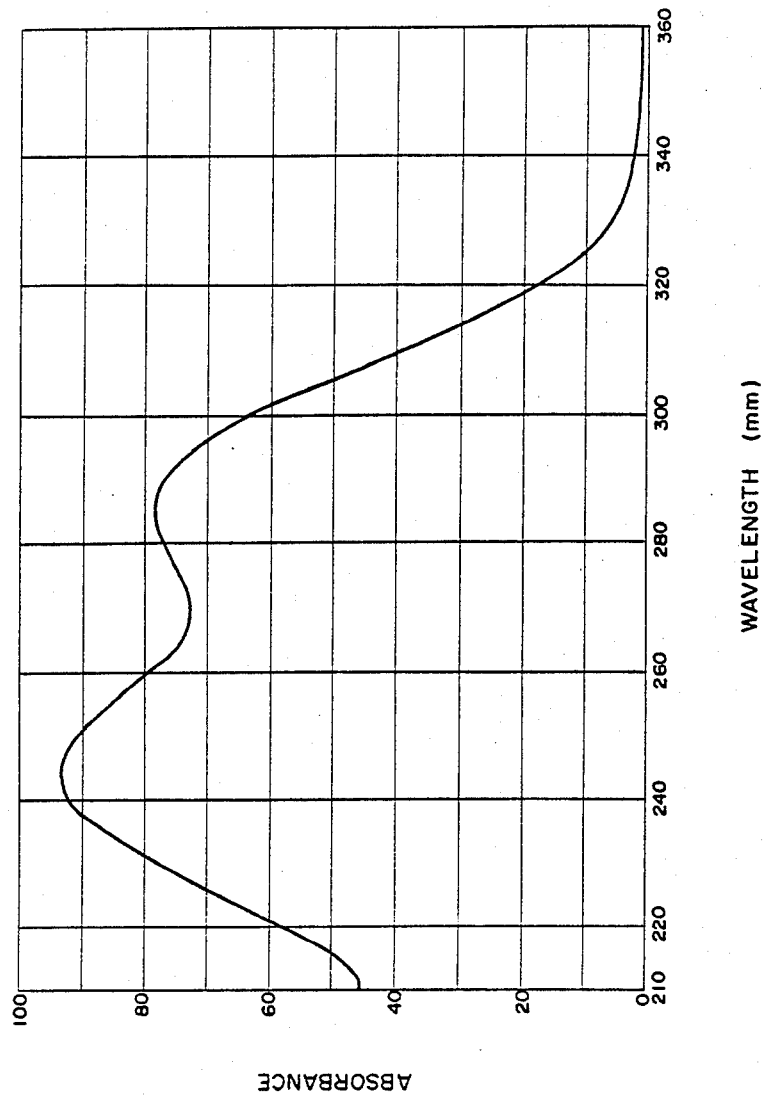
FIG. 1 depicts the UV spectrum of C-19393 E$_5$.

Production of Antibiotic C-19393 E$_5$ in accordance with this invention is carried out using a microorganism belonging to the genus Streptomyces which is capable of elaborating C-19393 E$_5$. Such a microorganism will hereinafter be referred to briefly as a C-19393 E5-producing strain.

As an example of such C-19393 E$_5$- producing strain, there may be mentioned Streptomyces sp. C-19393 [FERM-P No. 4774, IFO 13886, ATCC 31486 NARL 1503]. This microorganism was subsequently identified as *Streptomyces griseus subsp. cryophilus* C-19393]. Hereinafter, this strain will sometimes be referred to briefly as the C-19393 strain. The C-19393 strain elaborates Antibiotic C-19393 S$_2$ and Antibiotic C-19393 H$_2$ [German Offenlegungsschrift No. 3003624] as well.

In order that the present invention may be carried into practice more advantageously, it is desirable to use a strain belonging to the genus Streptomyces which is capable of elaborating C-19393 H$_2$ and which would not give normal growth on a medium containing inorganic sulfates as exclusive sources of sulfur but gives normal growth in the presence of at least a member selected from the group consisting of thiosulfates, cysteine and methionine. The inorganic sulfates mentioned as sources of sulfur include alkali metal sulfate (e.g. Na$_2$SO$_4$, K$_2$SO$_4$), alkaline earth metal sulfate (e.g. CaSO$_4$, MgSO$_4$), heavy metal sulfate (e.g. FeSO$_4$, Fe$_2$(SO$_4$)$_3$, CuSO$_4$, ZnSO$_4$, NiSO$_4$), ammonium sulfate and other sulfates which would yield SO$_4^{--}$ ions and which would not inhibit the growth of microorganism. On the other hand, the thiosulfates may for example be sodium thiosulfate, potassium thiosulfate, ammonium thiosulfate, etc.

The test of growth of the C-19393 E$_5$-producing strain is performed on synthetic agar medium. The screening procedure may for example be as follows. First, two kinds of media are prepared. Medium (1): 10 g of glycerol, 1 g of L-asparagine, 1 g of dipotassium phosphate, 0.2 g of magnesium sulfate, 20 g of agar (Difco Lab., U.S.A.) and 1000 ml of distilled water (pH 7.1). Medium (2): the same medium as (1) *plus* 50 mg of sodium thiosulfate, L-cysteine or L-methionine. Each medium is steam-sterilized and put into a Petri dish. After the agar is set, the dish is inoculated with a suspension of the spores or mycelia of the C-19393 H$_2$-producing strain (When any carry-over of growth factors from the preculture is suspected, the spore suspension is washed with distilled water once) and the inoculated dish is incubated at 28° C. for 2 to 7 days. There will be an abundant growth on plate (1), whereas either no growth or only a sparse growth will be found on plate (2).

As examples of useful C-19393 E$_5$-producing strains, there may be mentioned *Streptomyces griseus subsp. cryophilus* K-4, K-101 and SR-135 (hereinafter sometimes referred to briefly as K-4 strain, K-101 strain and SR-135 strain, respectively) which have been obtained by subjecting the parent C-19393 strain to mutagenic treatment. These and other mutants can be derived, for example by the following methods.

(A) Selection from among the mutants requiring for growth at least a member selected from the group consisting of thiosulfates, cysteine and methionine.

The suspension of spores prepared by mutagenic treatment of the C-19393 strain is spread on Bennet's agar medium, for instance, to cultivate colonies (about 10 to 100 per plate). These colonies are replicated onto (i) a minimal medium [e.g. 10 g of glycerol, 1 g of L-asparagine, 1 g of dipotassium phosphate, 0.2 g of magnesium sulfate, 20 g of agar and 1000 ml of distilled water; pH 7.1] and (ii) a screening medium [the minimal medium supplemented with 50 to 500 mg of thiosulfate, L-cysteine or L-methionine] and each of the media is incubated at 24°–30° C. for 2–5 days. The mutant which gives as good growth as the parent strain on the screening medium but gives either no growth or only sparse growth on the minimal medium is selected. The mutant is cultured on a liquid medium and its elaboration product is examined. The desired mutant strain is accordingly selected.

(B) Selection of a selenate-resistant strain

The suspension of spores of the C-19393 strain subjected to mutagenic treatment is spread on a minimal agar medium containing 0.025 to 0.2% (preferably 0.05–0.2%) of a selenate (e.g. sodium selenate, ammonium selenate) at a high concentration and incubated at 24°–30° C. for 2–14 days. If the concentration of the selenate is low, a thin growth will be formed all over the agar surface. The strain giving a large colony on the plate is picked and reinoculated on an agar medium containing the selenate in the same concentration to purify the colony. The resultant grown colony is picked and incubated on a slant medium. The selenate-resistant strain thus obtained is subjected to liquid culture and its elaboration product is examined. In this manner, the contemplated mutant strain can be selected.

The mechanism by which the desired mutant strain can be obtained with efficiency by method (A) or (B) remains yet to be fully elucidated but it is likely that a defect was produced in the organism in connection with the incorporation or metabolism of inorganic sulfate ions.

The mutagenic treatment mentioned hereinbefore may be any suitable chemical or physical treatment that is known, such as UV light irradiation and a treatment with NTG(N-methyl-N'-nitro-N-nitrosoguanidine), ethyl methanesulfonate, nitrous acid or the like.

The three strains of *Streptomyces griseus* subsp. *cryophilus* K-4, K-101 and SR-135 have been deposited with Institute for Fermentation, Osaka, Japan, Fermentation Research Institute, Agency of Industrial Science and Technology, Tsukuba, Japan, The American Type Culture Collection, U.S.A. and the U.S. Department of Agriculture, Northern Regional Research Laboratory, U.S.A. under the following IFO numbers, FERM-P numbers and ATCC number since Oct. 16, 1980, Oct. 17, 1980, Oct. 28, 1980, and Aug. 2, 1982 respectively.

|        | IFO   | FERM-P No. | ATCC  | NRRL  |
|--------|-------|------------|-------|-------|
| K-4    | 14089 | 5750       | 31740 | 15115 |
| K-101  | 14090 | 5751       | 31741 | 15116 |
| SR-135 | 14091 | 5752       | 31742 | 15117 |

The bacteriological characteristics of these strains, except for biochemical properties and antibiotic producing ability, are substantially similar to those of the parent C-19393 strain. However, compared with the parent strain, the K-4 strain features a considerably sparse production of aerial mycelium.

(a) Morphological characteristics

The aerial mycelium, about $1\mu$ in length, extends from a well-branched substrate mycelium and branches out monopodially to present side branches each carrying straight or slightly curved chains of spores in the manner of rectus flexibilis. The spores are cylindrical ($0.35$–$0.55\mu \times 0.7$–$1,4\mu$), each having a smooth surface. There are no other special organs such as spherical sporangium, flagellum, sclerotium, etc.

(b) Cultural characteristics

The cultural characteristics of the present strain on various media are shown in Table 1. Unless otherwise indicated, these are observations after incubation at 28° C. for 2 weeks.

TABLE 1

| Medium | Growth | Aerial Mycelium | Reverse | Soluble Pigment |
|--------|--------|-----------------|---------|-----------------|
| (1) Sucrose nitrate agar | Moderate | White | Colorless | None |
| (2) Glucose asparagine agar | Slight | White | Colorless | None |
| (3) Glycerin asparagine agar | Moderate | White | Colorless | None |
| (4) Starch agar | Moderate | None | Ocher | None |
| (5) Nutrient agar | Moderate | White | Ivory | None |
| (6) Tyrosine agar | Moderate | None | Colorless | None |
| (7) Yeast malt agar | Moderate | None | Grayish yellow | None |
| (8) Oatmeal agar | Moderate | White | Colorless | None |

Note
Media (1), (2), (3), (4) and (6) were each supplemented with 50 mg/l of sodium thiosulfate.

(c) Physiological characteristics
(1) Temperature range for growth:
  lower limit: lower than 15° C.
  upper limit: 32° to 35° C.
  optimal temperature: 26.5° to 30° C.
(2) Gelatin: liquefied
(3) Starch: hydrolyzed
(4) Skim milk: peptonized but not coagulated
(5) Melanoid pigment:
  Tyrosine agar: not produced
  Peptone yeast extract iron agar: nor produced
(6) The carbohydrate assimilation spectrum of the strain (Pridham-Gottlieb agar with 50 mg/l of sodium thiosultate) is shown in Table 2.

TABLE 2

| Carbon Sources | Assimilation |
|----------------|--------------|
| Glycerin | + |
| i-Inositol | ± |
| D-Mannitol | − |
| D-Xylose | ± ~ + |
| L-Arabinose | ± ~ + |
| D-Glucose | + |
| D-Galactose | + |
| D-Fructose | + |
| Maltose | + |
| Sucrose | − |
| Rhamnose | + |
| Raffinose | − |
| Starch | + |
| Cellulose | ± |
| Control (No addition) | − |

−: no growth;
+: growth
±: doubtful growth;

(d) Biochemical characteristics

All of K-4, K-101 and SR-135 strains require for growth at least one of sodium thiosulfate, cysteine and methionine.

The cultivation of such strain for the production of C-19393 $E_5$ in accordance with this invention is conducted using a culture medium containing nutrients which the strains may utilize for growth. Among useful medium components are such sources of carbon as glucose, starch, glycerin, dextrin, sucrose, millet jelly, molasses, etc. and such sources of nitrogen as meat extract, dried yeast, yeast extract, soybean flour, corn steep liquor, wheat germs, cottonseed flour, ammonium sulfate, ammonium nitrate, etc. As additional components, such inorganic salts as calcium carbonate, sodium chloride, potassium chloride, phosphates, etc. as well as organic and inorganic components which will either assist in the growth of the strains or contribute to an increased output of C-19393 $E_5$ may be incorporated into the culture medium.

If necessary, heavy metals such as ferrous sulfate, copper sulfate, etc. and vitamins such as vitamin $B_l$, biotin, etc. are also added to the medium. It will also be beneficial to incorporate in the medium an antifoaming agent or surfactant such as silicone oil or a polyalkylene glycol ether. Other organic and inorganic substances which aid the growth of microorganism and promote the production of C-19393 $E_5$ can be added to the medium in suitable amounts.

Cultivation of the strain can be conducted by the conventional procedure for the microbial production of antibiotics using solid or liquid media. When, for example, a liquid medium is employed, cultivation may be carried out by any of such methods as stationary culture, stir culture, shake culture, aerobic culture and so on, although submerged aerobic culture is preferable. The preferred range of cultivation temperature is about 15° C. to about 32° C., the preferred range of medium pH is about 4 to about 8, and the cultivation time is about 8 to about 168 hours, preferably about 24 to about 144 hours.

Since C-19393 $E_5$ is mostly produced extracellularly, it is a preferred procedure to subject the culture broth to centrifugation or filtration to obtain a supernatant and isolate the desired antibiotic from the supernatant. It is, however, also possible to isolate and purify the antibiotic directly from the culture broth.

The potency assay of the product thus obtained may be performed against *Comamonas terrigena* IFO 13299 as the test organism and using C-19393 $E_5$-producing strain as the standard by the cylinder-plate method or by the paper employing a bouillon agar and TSA (trypticase soy agar; Baltimore Biologicals, Co., Ltd., U.S.A.) as the assay medium.

For the isolation of C-19393 $E_5$, the procedures conventionally employed for the harvest and isolation of microbial metabolites can be utilized to advantage. For example, since C-19393 $E_5$ is a water-soluble acid substance and is mostly produced extracellularly, it is generally isolated by subjecting the culture broth to centrifugation or filtration to separate the microbial cells and isolating and purifying the activity from the filtrate. Thus, for example, various separation methods such as those utilizing differential solubilities or distribution coefficients in solvents, differential rates of precipitation or differential adsorption affinities, ion-exchange chromatography, molecular sieve chromatography, concentration in vacuo, lyophilization, etc. can be utilized in a suitable combination and in any order or in repetition. By way of illustration, activated carbon, adsorbent resins, anion-exchange resins (anionic type), cellulose powder, silica gel, etc., as well as those supports functioning as molecular sieves can be employed. Elution from such adsorbents or supports may be effected with an eluent appropriate to the particular adsorbent or carrier used, such as water-soluble organic solvents such as acetone, methanol, ethanol, propanol, butanol, isopropyl alcohol, isobutanol, etc., aqueous solutions of such water-soluble solvents, acid, alkali or buffer solutions, or aqueous solutions of inorganic or organic salts.

More specifically, the first step in the separation and purification procedure comprises filtering the culture broth in the presence of a filter aid to remove the microbial cells. Since Antibiotic C-19393 $E_5$ is an acidic compound, the $Cl^-$ or $ACO^-$ forms of anion-exchange resins such as Amberlite IRA-400, 402, 410 (Rohm and Haas Co., U.S.A.), Dowex-1 (Dow Chemical Co., U.S.A.) and Diaion SA-21 A and C (Mitsubishi Kasei K.K., Japan) can be utilized to advantage in further purification. In this case, the adsorbed antibiotic is eluted with an aqueous solution of sodium chloride or a buffer solution. The eluate is then passed through a high-porous adsorbent resin, e.g. Diaion HP-20 (Mitsubishi Kasei K.K., Japan), and the adsorbed activity is eluted with water. Desalination of this eluate is carried out by activated carbon chromatography using an aqueous alcohol or the like as an eluent. The eluate is concentrated at reduced pressure and low temperature to remove the alcohol, followed by addition of sodium chloride to a concentration of 5%. The solution is subjected again to HP-20 chromatography and elution is carried out with a 5% aqueous solution of sodium chloride, further followed by desalting with activated carbon. The eluate obtained using an aqueous alcohol or the like is concentrated at low temperature to remove the alcohol or the like. The residue is passed through a resin such as Diaion WA-30 (acetate-form, Mitsubishi Kasei K.K., Japan) and elution is carried out with a 1M aqueous solution of sodium chloride. The eluate is desalted with activated carbon and, as the eluent, aqueous isobutanol. Satisfactory results can be obtained if dilute aqueous ammonia is added to the eluent so as to carry out the elution under neutral or slightly basic conditions. The eluate containing the antibiotic activity is concentrated under reduced pressure, acetone is then added to the residue, and the resulting precipitate is recovered by filtration. This powdery precipitate can be further purified by column chromatography, for example by using an adsorbent resin HP-20 or XAD (Rohm and Haas Co., U.S.A.) and DEAE or QAE-Sephadex (Cl-form, Pharmacia, Sweden) in combination. Thus, the above powder is dissolved in a small amount of water and chromatographed on a column of XAD-II, elution being carried out with water. The active fractions are pooled and concentrated, and the concentrate is further passed through a QAE-Sephadex-25 ($Cl^{31}$-form). Elution is carried out with 0.04M phosphate buffer and the eluate is desalted by activated carbon chromatography in the same manner as described above. The eluate is concentrated and the concentrate is chromatographed on a column of HP-20, elution being carried out with water. The fractions giving a single peak on liquid chromatography described hereinafter are pooled and concentrated to dryness at reduced pressure and low temperature. To the concentrate is added acetone, for instance, whereby C-19393 $E_5$ is obtained. This compound is capable of forming metal or ammonium salts. The metal salts include sodium, potassium, lithium and other salts.

The physical and chemical properties of the sodium salt of C-19393 $E_5$ prepared in accordance with Example 1, which appears hereinafter, are as follows.
(1) Appearance: White powder
(2) Thin-layer chromatography:
Cellulose f (Tokyo Kasei Co., Ltd., Japan) and a developer solvent system of n-propanol/water (4:1): Rf=0.57±0.1.
DEAE-cellulose (Tokyo Kasei Co., Ltd., Japan) and a developer solvent system of 0.02M aqueous NaCl/n-propanol (1:1): Rf=0.44±0.1.
(3) High-voltage paper electrophoresis: Electrophoretic mobility on Whatman No. 1 paper [W and R Balston, Ltd., England] in 0.02M phosphate buffer (pH 6.9) at a potential gradient of 45 V/cm for 50 minutes: 11 cm±2 cm toward the anode.
(4) Molecular formula: $C_{13}H_{15}N_2O_6SNa$
(5) High-performance liquid chromatography (Waters Associates Inc., U.S.A.): HPLC on Microbondapak $C_{18}$ using 0.02M phosphate buffer with 4% methanol (pH 6.3) and 0.02M phosphate buffer with 6% methanol (pH 6.3) at the flow rate of 2 ml/min. showed the retention times of 4.2 min. and 2.8 min., respectively.

(6) Ultraviolet absorption spectrum: The UV spectrum of C-19393 $E_5$ in aqueous solution is depicted in FIG. 1 and the maximum values are as follows: $\lambda_{max}^{H_2O}(E_{1\ cm}^{1\%}) = 244 \pm 2$ nm $(374 \pm 20)$ and $286 \pm 2$ nm $(313 \pm 20)$.

Figure 2:
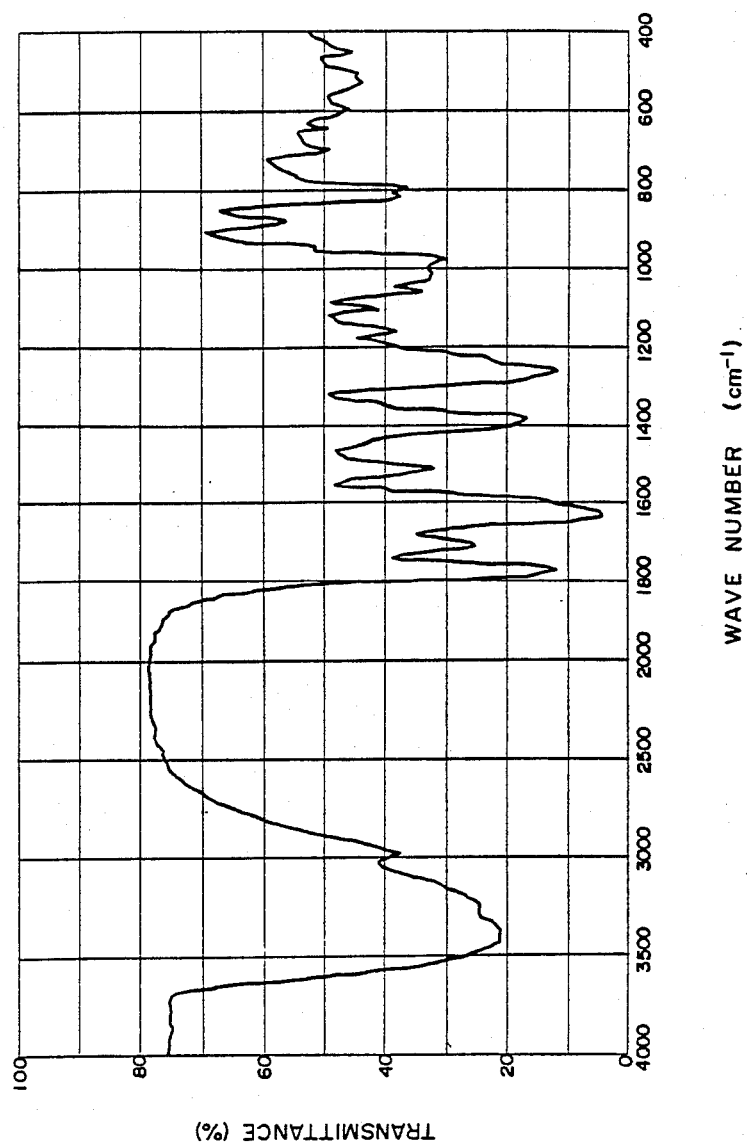
FIG. 2 depicts the IR spectrum of C-19393 E$_5$.

(7) Infrared absorption spectrum: The IR spectrum (KBr disk) of C-19393 $E_5$ is depicted in FIG. 2. Main absorptions (wave-numbers) are as follows: 3400, 2980, 1765, 1700, 1620, 1505, 1380, 1260, 1160, 1100, 1055, 1000, 970, 940, 870, 810, 790, 690, 640, 600, 520, 450 (cm$^{-1}$)

(8) Circular dichroism spectrum (in $H_2O$): The spectrum shows a positive Cotton effect at 234 nm and negative Cotton effects at 210, 260 and 290 nm.

(9) Color reactions:
Ehrlich: positive
Potassium permanganate: positive
Ninhydrin: negative

(10) Solubility: Readily soluble in water; insoluble in benzene, ethyl acetate and acetone.

(11) Proton magnetic resonance spectrum: The characteristic chemical shifts of C-19393 $E_5$ (sodium salt) in $D_2O$ at 100 MHz are as follows:

1 ca. 1.38 ppm, doublet (J=ca. 6 Hz)

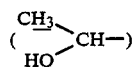

2 ca. 2.16 ppm, sharp singlet ($CH_3$—CO—NH—)
3 ca. 2.8-4.0 ppm, 2H and 1H, multiplet

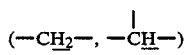

4 ca. 4.0-4.6 ppm, 2H, multiplet

5 ca. 6.44 ppm, doublet (J=14 Hz) (—N—C$\underline{H}$=)
6 ca. 7.60 ppm, doublet (J=14 Hz) (—S—C$\underline{H}$=)

Based on the above physical and chemical properties, C-19393 $E_5$ is assumed to be a compound having the structural formula (I).

The properties of C-19393 $E_5$ described above are in good accord with those of the compound obtained by oxidation of Epithienamycin B.

The biological properties of C-19393 $E_5$ are as follows. The antibacterial spectrum of the sodium salt of C-19393 $E_5$ is shown in Table 3. It is apparent from the data that C-19393 $E_5$ is a broad spectrum antibiotic which is highly active against both gram-positive and gram-negative bacteria.

TABLE 3

| Antimicrobial Spectrum of Antibiotic C-19393 $E_5$ Sodium Salt | |
|---|---|
| Test Organism | Minimum Inhibitory Concentration (μg/ml) |
| Escherichia coli NIHJ | 0.78 |
| Salmonella typhimurium IFO 12529 | 0.78 |
| Klebsiella pneumoniae IFO 3317 | 6.25 |

TABLE 3-continued

| Antimicrobial Spectrum of Antibiotic C-19393 $E_5$ Sodium Salt | |
|---|---|
| Test Organism | Minimum Inhibitory Concentration (μg/ml) |
| Proteus vulgaris IFO 3988 | 1.56 |
| Proteus mirabilis ATCC 21100 | 3.13 |
| Serratia marcescens IFO 12648 | 6.25 |
| Alcaligenes faecalis IFO 13111 | 1.56 |
| Pseudomonas aeruginosa IFO 3080 | 6.25 |
| Comamonas terrigena IFO 13299 | 0.78 |
| Staphylococcus aureus 209P | 0.78 |
| Sarcina lutea IFO 3232 | 0.2 |
| Bacillus subtilis PCI 219 | 0.78 |

Note
Medium: Bouillon agar

As shown in Table 3 above, C-19393 $E_5$ obtained in accordance with the present invention has strong antimicrobial activity against gram-positive and gram-negative bacteria and, thus, can be used in the treatment of bacterial infections in mammalian animals (e.g. mouse, rat, dog, human being) and domestic fowls (e.g. poultry, duck).

To use C-19393 $E_5$ as a drug for the treatment of Escherichia coli infections, for instance, it can be formulated into an injectable solution in physiological saline and administered parenterally, e.g., subcutaneously or intramuscularly at the daily dose level of 0.1 to 50 mg/kg or preferably 0.5 to 20 mg/kg. It may also be formulated into an encapsulated preparation together with lactose, for instance, and administered in the daily dose of 1 to 100 mg/kg or preferably 5 to 50 mg/kg (as C-19393 $E_5$).

C-19393 $E_5$ can be used as a disinfectant. For example, it can be dissolved in distilled water to a concentration of 0.01 to 0.1 w/v % so as to provide a liquid disinfectant or formulated with a base such as vaseline or lanolin to provide an ointment containing 0.2 to 20 mg or preferably 1 to 10 mg of C-19393 $E_5$ per gram. The solution and ointment can each be externally applied as a bactericide or disinfectant for the extremities, eyes, ears, etc. of said animals.

Antibiotic C-19393 $E_5$ is also a very promising compound as an intermediate for the synthesis of new pharmaceutical agents. The aqueous solution of C-19393 $E_5$ is stable in the neutral pH region.

EXPERIMENT 1

The spores ($10^7$/ml) of Streptomyces griseus subsp. cryophilus C-19393 (IFO 13886, ATCC 31486) were suspended in 10 ml of 0.05 M tris-maleic acid buffer (pH 8.9). To the suspension was added N-methyl-N'-nitro-N-nitrosoguanidine at the rate of 1 mg/ml and, then, the mixture was shaken at 30° C. for 60 minutes. The reaction mixture was subjected to centrifugation (10,000×g, 15 min.), to remove the supernatant, followed by addition of 10 ml of sterile distilled water to the residue to wash the spores well. The mixture was again centrifuged to collect the spores. The spores thus obtained were suspended in 10 ml of sterile distilled water. The suspension was diluted with sterile distilled water to $10^2$–$10^4$ of spores. A 0.1 ml each portion of the suspension was spread on Bennet's agar medium (composition: 1 g of yeast extract, 1 g of meat extract, 2 g of NZ amine A, 10 g of glucose, 1000 ml of distilled water and 20 g of agar; pH 7.1) and incubated at 28° C. for 4 days.

The 20 plates were selected from among those cultivated with about 20-100 colonies per plate. These colonies were inoculated by the replicate method onto a minimal medium (composition: 10 g of glycerol, 1 g of L-asparagine, 1 g of dipotassium phosphate, 0.2 g of magnesium sulfate, 20 g of agar and distilled water; pH 7.1) and a screening medium A (the minimal medium supplemented with 50 mg/l of L-cysteine) and each of the media was incubated at 28° C. for 3 days. Another 20 plates were selected from among those cultivated with about 20–100 colonies per plate. These colonies were replicated on a minimal medium (the same as said composition) and a screening medium B (the minimal medium supplemented with 50 mg/l of sodium thiosulfate) and each of the media was incubated at 28° C. for 3 days.

In comparison of the growth of colonies on the minimal medium with that on the screening medium, K-4 strain was selected from colonies which gave only sparse growth on the minimal medium but gave good growth on the screening medium A, and K-101 strain was selected from colonies which gave abundant growth on the screening medium B.

These strains were purified on the respective screening media.

The strains thus obtained were incubated on minimal media containing sodium thiosulfate, L-cysteine or L-methionine in various concentrations at 28° C. for 4 days. The results of growth are shown in Table 4.

TABLE 4

| Compound | Strain | \multicolumn{7}{c}{Concentration of Compound (mg/ml)} |
|---|---|---|---|---|---|---|---|---|
| | | 0 | 3.125 | 6.25 | 12.5 | 25 | 50 | 100 |
| Sodium thiosulfate | K-4 | ∓ | + | + | ++ | +++ | +++ | +++ |
| | K-101 | ∓ | ± | ± | ± | + | ++ | +++ |
| | C-19393 | +++ | +++ | +++ | +++ | +++ | +++ | +++ |
| L-Cysteine | K-4 | ∓ | + | + | ++ | +++ | +++ | +++ |
| | K-101 | ∓ | + | ++ | +++ | +++ | +++ | +++ |
| | C-19393 | +++ | +++ | +++ | +++ | +++ | +++ | +++ |
| L-Methionine | K-4 | ∓ | + | ++ | ++ | +++ | +++ | +++ |
| | K-101 | ∓ | + | ++ | +++ | +++ | +++ | +++ |
| | C-19393 | +++ | +++ | +++ | +++ | +++ | +++ | +++ |

− No growth,
+ Growth,
∓ Sparse growth,
++ Good growth,
± Moderate growth
+++ Abundant growth on a slant medium. In this manner, SR-135 strain was selected.

SR-135 and C-19393 strains were incubated on a minimal medium containing sodium thiosulfate, L-cysteine or L-methionine at 28° C. for 4 days.

The results of growth are shown in Table 5.

TABLE 5

| Compound | Strain | \multicolumn{7}{c}{Concentration of Compound (mg/l)} |
|---|---|---|---|---|---|---|---|---|
| | | 0 | 3.125 | 6.25 | 12.5 | 25 | 50 | 100 |
| Sodium thiosulfate | SR-135 | ± | + | ++ | ++ | +++ | +++ | +++ |
| | C-19393 | +++ | +++ | +++ | +++ | +++ | +++ | +++ |
| L-Cysteine | SR-135 | ± | ++ | +++ | +++ | +++ | +++ | +++ |
| | C-19393 | +++ | +++ | +++ | +++ | +++ | +++ | +++ |
| L-Methionine | SR-135 | ± | ++ | +++ | +++ | +++ | +++ | +++ |
| | C-19393 | +++ | +++ | +++ | +++ | +++ | +++ | +++ |

(± ~ +++ have the same meaning as defined in Table 4)

The growths (28° C., 7 days incubation) of strains on the minimal medium containing sodium selenate in various concentrations are shown in Table 6.

TABLE 6

| Strain | \multicolumn{7}{c}{Compound Sodium selenate (mg/l)} |
|---|---|---|---|---|---|---|---|
| | 0 | 62.5 | 125 | 250 | 500 | 1000 | 2000 |
| C-19393 | +++ | +++ | ++ | ± | ∓ | − | − |
| SR-135 | + | ++ | ++ | ++ | ++ | ++ | + |

(− ~ +++ have the same meaning as defined in Table 4)

As shown in Table 6, the growth of C-19393 strain was inhibited by addition of sodium selenate not less than 250 mg/l.

The following examples are intended to illustrate the invention in further detail and should by no means be construed as limiting the scope of the invention. In these examples, all percents are by weight/volume unless otherwise indicated.

EXAMPLE 1

EXPERIMENT 2

The suspension of spores prepared by mutagenic treatment similar to Experiment 1 was diluted to $10^0$–$10^2$ of spores. A 0.1 ml portion of the suspension was spread on a plate of agar medium which was added to a minimal medium (composition: same as Experiment 1) with 500 mg/l of sodium selenate and incubated at 28° C. for 7 days. A scant growth was observed all over the agar surface. The strain giving a large colony on the plate was selected and reinoculated on an agar medium containing sodium selenate to purify the colony. The resultant grown colony was picked out and incubated Streptomyces sp. C-19393 (IFO 13886, ATCC 31486) was grown on 200 ml of a medium comprising 2% oatmeal, 2% tomato paste, 0.2% bovril (Bovril, England) and 2% agar (pH 7.0) in a one-liter conical flask to cause sporulation. The spores were suspended in sterile water to a viable count of $1.2 \times 10^8$/ml. The spore suspension was diluted 10-fold with sterile water and 1 ml of the dilution was used to inoculate 40 ml of a seed medium in a 200-ml conical flask, which was incubated at 28° C. on a rotary shaker for 2 days. The resulting culture fluid was transferred to a 2-liter Sakaguchi shake flask containing 500 ml of the same seed medium as above and cultivated at 28° C. on a reciprocating shaker for 2 days. The culture was further transferred to a 200-liter stainless steel fermenter containing 100 liters of said seed medium supplemented with 50 ml of Actocol (Takeda Chemical Industries, Ltd., Japan) and cultivated at 28° C., 70 liters/min aeration and 150 r.p.m. for 2 days. Then, the culture was transferred to a 6-m$^3$ fermenter containing 4 m$^3$ of a main culture medium and grown at 30° C., 2800 liters/min. aeration and 150 r.p.m. for 3 days. The seed medium mentioned above contains per liter 20 g of glucose, 30 g of soluble starch, 10 g of raw soybean flour, 10 g of corn steep liquor, 5 g of Polypepton (Daigo Nutritive Chemicals, Ltd., Japan), 3 g of sodium chloride and 5 g of precipitated calcium carbonate (adjusted to pH 7.0 before sterilization). The main culture medium contained per liter 30 g of glucose, 30 g of soluble starch, 15 g of raw soybean flour, 15 g of cottonseed flour, 0.25 g of potassium dihydrogen phosphate, 0.6 g of potassium monohydrogen phosphate, 0.002 g of cobalt chloride and 0.5 g of Actocol (adjusted to pH 7.0 before sterilization). These media were all steam-sterilized at 120° C. for 20 minutes.

The fermentation broth thus obtained was filtered with Hyflo-Supercel (Johns Manville Co., U.S.A.) and the filtrate (4000 l) was adjusted to pH 6.3 and passed through a column of Amberlite IRA-402 (Cl$^-$-form). After washing the column with 200 l of 0.02 M aqueous NaCl, elution was carried out with 1000 l of 1.5 M NaCl. The eluate was passed through a column of HP-20 (70 l) and the antibiotic activity was eluted with 280 l of water. The eluate was passed through a column of activated carbon (15 l) and after washing the column with 45 l of water, the antibiotic activity was eluted with 60 l of 7% isobutanol. The eluate was concentrated to 10 l and 500 g of NaCl was added to the residue. The mixture was passed through a column of HP-20 (6 l) and elution was carried out with 36 l of 5% NaCl. The eluate was passed through a column of activated carbon (3 l). The column was washed with 7.5 l of water and, then, elution was carried out with 8% isobutanol. The eluate was concentrated to 8 l under reduced pressure and, then, passed through a column of WA-30 (acetate-form) (500 ml). The column was washed with 2.5 l of 0.2 M acetic acid-sodium acetate buffer and the activity was eluted with 5 l of 1 M NaCl in the same buffer.

The eluate was passed through a carbon column (500 ml). After the column was washed with 5% NaCl, elution was carried out with 2.5 l of 5% aqueous NaCl-methanol (4:1). The methanol was distilled off under reduced pressure and the residue was passed again through a carbon column (200 ml). The column was washed with 600 ml of H$_2$O and 600 ml of 20% aqueous methanol, followed by elution with 600 ml of 8% isobutanol. The eluate was concentrated under reduced pressure, the residue was treated with acetone and the resultant powder was collected (580 mg). The powder was dissolved in a small amount of water and passed through a column of Amberlite XAD-II (100–200 mesh) (360 ml). Fractional elution was carried out with water and the active fractions were pooled, concentrated to dryness, and treated with acetone to give 100 mg of powder. The powder was dissolved in a small amount of water and passed through a column of QAE-Sephadex A-25 (Cl$^-$-form) (40 ml). Elution was carried out with 0.04 M phosphate buffer and the active fractions were pooled and subjected to liquid chromatography as described hereinbefore. The fractions giving a single peak were pooled and passed through a column of 10 ml activated carbon. The carbon column was washed with 30 ml of water and the activity was eluted with 50 ml of 8% isobutanol. The eluate was concentrated to dryness and acetone was added to the concentrate. The above procedure gave 20 mg of C-19393 E$_5$ sodium salt.

Example 2

From slant cultures of Streptomyces griseus subsp. Cryophilus K-4, (IFO 14089, ATCC 31740), K-101 (IFO 14090, ATCC 31741) and SR-135 (IFO 14091, ATCC 31742) and Streptomyces sp. C-19393 (IFO 13886, ATCC 31486), a loopful each was taken and inoculated into 40 ml of a seed culture medium in a 200 ml conical flask. The flask was incubated on a rotary shaker at 28° C. for 2 days. A 1 ml portion of the culture was transferred to a 200 ml conical flask containing 40 ml of a main culture medium and cultivated at 28° C. for 4 days. The seed culture medium contained per liter 20 g of glucose, 30 g of soluble starch, 10 g of raw soybean flour, 10 g of corn steep liquor, 5 g of Polypepton, 3 g of NaCl and 5 g of precipitated calcium carbonate (adjusted to pH 7.0 before sterilization). The main culture medium contained per liter 15 g of glucose, 45 g of soluble starch, 15 g of cottonseed flour, 15 g of corn steep liquor, 0.25 g of potassium dihydrogen phosphate, 0.6 g of potassium monohydrogen phosphate and 0.002 g of cobalt chloride (adjusted to pH 7.0 before sterilization). All media were steam-sterilized at 120° C. for 20 minutes.

After the above cultivation, the cells are removed and the supernatant is assayed for C-19393 E$_5$. The results obtained in accordance with the above procedures are shown below.

| Strain | C-19393 E$_5$ in supernatant ($\mu$g/ml) |
| --- | --- |
| K-4 | 3 |
| K-101 | 2 |
| SR-135 | 1 |
| C-19393 (parent) | 0.2 |

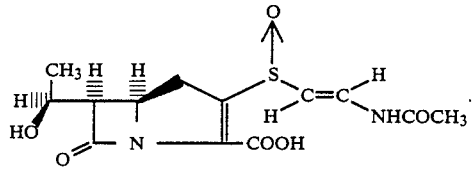

What we claim is:

1. A pharmaceutically acceptable salt of antibiotic C-19393 E$_5$ of the formula